(12) United States Patent
Price et al.

(10) Patent No.: US 8,998,903 B2
(45) Date of Patent: Apr. 7, 2015

(54) WEDGE OPENING OSTEOTOMY PLATE

(75) Inventors: James Price, Stow, OH (US); Bryan D. Den Hartog, Rapid City, SD (US); Derek S. Lewis, Copley, OH (US); David B. Kay, Akron, OH (US); Michael C. McGlamry, Marietta, GA (US); Terry Philbin, Dublin, OH (US); Mark Scioli, Lubbock, TX (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 148 days.

(21) Appl. No.: 12/932,954

(22) Filed: Mar. 10, 2011

(65) Prior Publication Data

US 2012/0184959 A1 Jul. 19, 2012

Related U.S. Application Data

(60) Provisional application No. 61/339,869, filed on Mar. 10, 2010.

(51) Int. Cl.
*A61B 17/56* (2006.01)
*A61B 17/58* (2006.01)
*A61B 17/80* (2006.01)
*A61F 2/30* (2006.01)

(52) U.S. Cl.
CPC .......... *A61B 17/8095* (2013.01); *A61B 17/8009* (2013.01); *A61B 17/8047* (2013.01); *A61B 17/8061* (2013.01)

(58) Field of Classification Search
CPC ............. A01B 12/006; A61B 17/8009; A61B 17/8047; A61B 17/8061
USPC ....................................... 606/70, 71
See application file for complete search history.

(56) References Cited

U.S. PATENT DOCUMENTS

| | | | |
|---|---|---|---|
| 5,275,601 A | 1/1994 | Gogolewski et al. | |
| 6,837,905 B1 | 1/2005 | Lieberman | |
| 2002/0010513 A1 | 1/2002 | Schmieding | |
| 2004/0092929 A1 | 5/2004 | Zindrick | |
| 2004/0127908 A1* | 7/2004 | Roman et al. | 606/72 |
| 2004/0172028 A1 | 9/2004 | Roger | |
| 2005/0177245 A1 | 8/2005 | Leatherbury et al. | |
| 2005/0277933 A1 | 12/2005 | Wall et al. | |
| 2006/0173459 A1* | 8/2006 | Kay et al. | 606/69 |
| 2006/0235411 A1 | 10/2006 | Blain et al. | |
| 2006/0241609 A1 | 10/2006 | Myerson et al. | |
| 2009/0082770 A1 | 3/2009 | Worner et al. | |
| 2009/0177203 A1 | 7/2009 | Reiley | |
| 2009/0210010 A1 | 8/2009 | Strnad et al. | |
| 2009/0222047 A1 | 9/2009 | Graham | |
| 2009/0234359 A1 | 9/2009 | Onoue et al. | |
| 2009/0264935 A1 | 10/2009 | Imbert | |
| 2009/0306667 A1 | 12/2009 | Lee et al. | |
| 2009/0306724 A1 | 12/2009 | Leither et al. | |
| 2010/0324559 A1* | 12/2010 | Ralph et al. | 606/71 |

* cited by examiner

*Primary Examiner* — Kevin T Truong
*Assistant Examiner* — Christine Nelson
(74) *Attorney, Agent, or Firm* — Hudak, Shunk & Farine Co. LPA

(57) ABSTRACT

An orthopedic plate is designed for opening osteotomies and includes a contoured double tabbed or butterfly shaped plate portion which can accommodate selective fixation including locking, variable locking and non-locking. The plate also includes a centrally located osteotomy support that maintains the opening between bone segments at a spaced relationship. The support can be integral to the plate, or can be modular, i.e. a separate and adjustable segment which can be changed to accommodate the desired geometry of the osteotomy site.

17 Claims, 3 Drawing Sheets

SECTION A-A

WEDGE OPENING OSTEOTOMY PLATE

CROSS REFERENCE

This Application claims the benefit of priority under 35 U.S.C. §119 of U.S. Provisional Application Ser. No. 61/339,869, filed on Mar. 10, 2010, herein fully incorporated by reference.

FIELD OF THE INVENTION

The present invention relates to an orthopedic plate for use in osteotomies, or surgical procedures, which involve a surgical resection to correct the alignment of a bone or joint. In particular, the plate is designed for wedge opening osteotomies, which involve surgical removal of bone to allow for an opening or widening of a section which permits the desired realignment. The invention includes a contoured plate portion having holes that receive fixation means (i.e. screws), and a centrally located osteotomy support that maintains the opening between bone segments at a spaced relationship. The support can be integral to the plate, or can be modular, i.e. a separate and adjustable segment, which can be changed to accommodate the desired geometry of the osteotomy site and moved to aid in reduction of the bones at the site.

BACKGROUND OF THE INVENTION

An osteotomy is a surgical procedure involving the surgical resecting of bone to correct a misalignment that can be a result of trauma, stress induced deformation, or congenital issues that manifest as misalignment. Hallus vagus, (which involves a bunion at the base of the great toe) is a typical example of a deformity, which may be surgically corrected by an osteotomy procedure and for which the present invention may be used. The surgery involves realignment of the bones of the metatarsophalangeal joint and can include removing bone from either side of the joint area, and opening a wedge shaped area to realign the bones of the great toe with the metatarsal bones of the foot.

Examples of other surgical procedures for which the present invention might be useful include Cotton osteotomy, Evans osteotomy, lapidus bunionectomy, calcaneolocuboid fusion, talonavicular fusion, MTP fusion, cuboid fracture, metarsocunieforrn fusion, chevron osteotomy, Naviculo-cunebform fusion, Dwyer osteotomy, isolated TMT fusion, Navicular fracture, and Lisfranc fracture, radial corrections revisiting wrist fusions, tibial osteotomies, and even pediatric femoral and hip surgeries.

SUMMARY OF THE INVENTION

In accordance with the present invention an orthopedic plate is provided that is specifically configured for use in opening osteotomies, and more specifically is configured for use on a variety of small bones. The plate has a bilateral double tabbed footprint (i.e., the outline looking down at the top of the plate). The footprint is symmetrical about the short axis in the x-y direction looking down on the plate, and includes on either side of that axis a larger extension, tab, or wing, and a smaller extension, tab, or wing, each extension including an opening (i.e., a screw hole). The opening optionally includes locking means, such as internal threads, which can accommodate fixed angle locking means or variable locking means that enable the captured screw to be placed with its axis at a variable angle with respect to the opening, and subsequently to be locked at that angle. The plate resembles the shape of a butterfly with a longer set of wings flanking a shorter set of wings.

It is preferred that the plate is curved in the z-direction (i.e., the plane of the paper looking down on the outline of the plate) such that there is a radius of curvature on the bottom (i.e. the bone-facing) side of the plate. Thus, the plate can form a portion of a cylinder. More preferred for certain indication, the long axis of the plate (i.e., the axis which divides the larger set of extensions from the smaller set of extensions) is also curved or bent in the z direction, so that the plate forms a more complex geometry, such as a section of a torroid or a portion of a cylinder that is bent along the long axis (in the wall of the cylinder). The curve in the plate in the medial direction causes the screws in the openings on either side of the medial axis (perpendicular to the long axis) to be aligned so that their respective axes converge toward each other. The fact that the holes are located at different distances from the medial axis, which is enabled by the relative sizes of the larger extension, and the smaller extension, causes the same side screw axes to converge on the bottom side of the plate, but not to intersect such that impingement of the screws is inhibited, while pullout strength and bone support is improved by the convergent angle.

Preferably, the screw holes include locking means, which could, for example, include internal threads that mate with corresponding external threads on the head of the screw. Other fastening means, such as pegs, could also be used. It is further advantageous, if means are provided to allow for the use of variable locking means in the same screw holes. The present invention, advantageously contemplates the use of a variable locking means that fits mate with the locking screw holes of the plates, but present the option of either fixed angle locking or variable angle locking and even variable angle non-locking using a screw with an appropriately sized rounded or hemispherical head that rides on the threads of the locking screw hole, depending on the surgeon's preference for the individual indication.

The bottom side of the screw also includes a centrally located osteotomy support means. In a first embodiment of the invention, the support is integral to the plate and preferably includes one or more flange members that extend from the plate in the z direction. When there are multiple flange members, and preferably, a pair, they are parallel so as to form a channel along the long axis, or the medial axis for the in-growth of bone, but to provide initial support for the bone edges following the surgery. The flanges can extend in the direction of the long axis or perpendicular to that direction along the medial axis.

In a second embodiment, the osteotomy support can be modular. In this version of the invention, the support can be a separate piece that has a first member extending through a passageway (i.e., optionally a round opening or a slot with a keyhole) in the center of the plate. The first support member has a neck, which slides in the passageway, and a stop that is wider than the narrow portion of the passageway, but which can be inserted through the key of the passageway in order to allow for assembly. The first support member can be a screw with a round stop or can have a stop of a more complex shape, such as an ellipse, and is attached to the support means, which can be a block, a pair of flanges. The support means can be rotated by means of the first support member that extends beyond the top surface of the plate to cause distraction of bone members on either side of the osteotomy. Optionally, the first support means, particularly in the case of the elliptical shaped member may include a high friction surface about it's edge such as angled teeth, or ratcheting members that block the support from rotating back once it has been positioned to help maintain the position when the first member slides into the passage way when the support means is in the desired position.

DETAILED DESCRIPTION OF THE INVENTION

Figure 1:
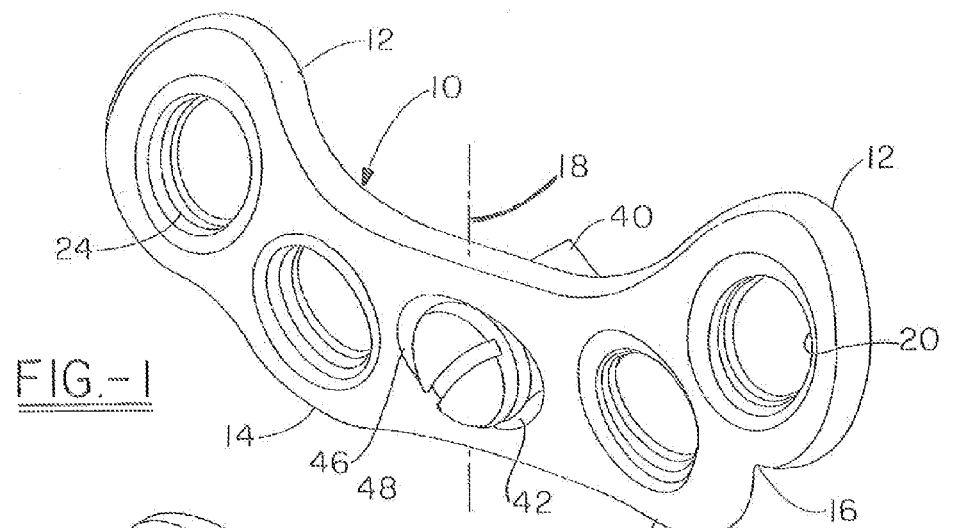
FIG. 1 is a front side view of a first embodiment of the osteotomy plate of the present invention showing a modular support.
Figure 8:
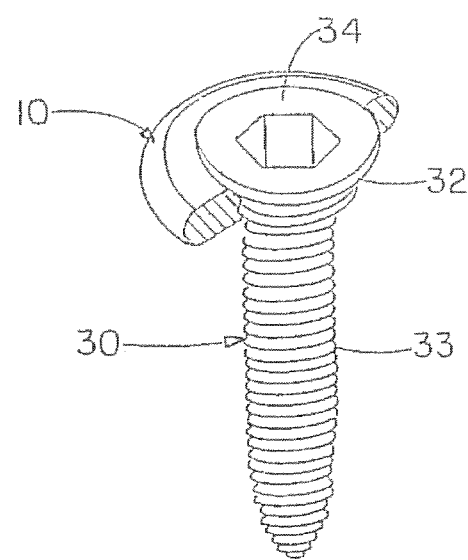
FIG. 8 is an illustration of a variable locking assembly that can be used with the present invention.

FIG. 1 shows a first embodiment of the osteotomy plate 10 in accordance with the invention, which has a plate member with a bilateral double tabbed footprint, with a first set of tabs 12 or wings flanking a second set of tabs 14 or wings with a slight incurve 16 between the tab members on either side of the medial axis 18. Each tab includes an opening 20 for a screw or other fastening means, which could, for example, include a peg or wire. The openings 20 also include internal threads 24 or other means to enable a locking relation to the screw 22, and optionally grooves 26 in the threads, which receive a drill guide (shown in FIG. 3). The threads of the openings receive the external threads on locking screws that can be used with the osteotomy plate. The openings also can receive variable locking assembly 30 as is shown in FIG. 8. Advantageously, the variable locking assembly 30 includes an externally threaded locking insert 32, which comprises a biocompatible material that is softer than the corresponding screw head 34 which is threaded into the locking insert at a desired angle so as to seat the screw 33 in the plate at a desired angle.

Figure 2:
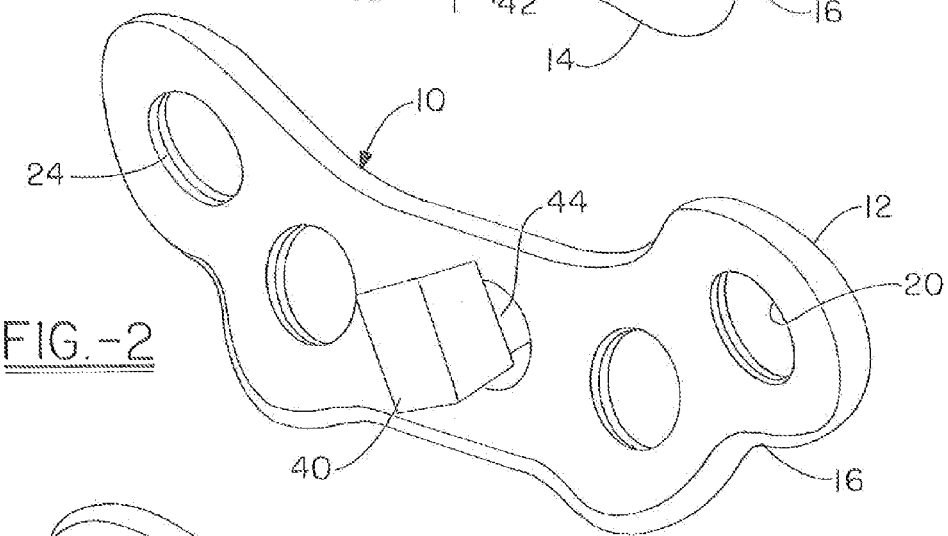
FIG. 2 is a back view of the osteotomy plate shown in FIG. 1.

The plate further includes a support member generally at 40, which can be integral to the plate member as is shown in the second embodiment, or can be modular as is illustrated in the first embodiment of the invention. In the modular version, the plate 10 includes a central opening 42 that receives a necked portion 44 of the support member 40. The necked portion is joined to a stop 46 that has at least a width that is wider than the central opening 42 so as to hold the support relative to the plate member 10. The stop can be a simple screw having a circular or round head 48 as is shown in FIGS. 1-3, or can be a more complex shape such as the ratcheting ellipse version 50 shown with an elliptical slot 51 in FIG. 4.

Figure 3:
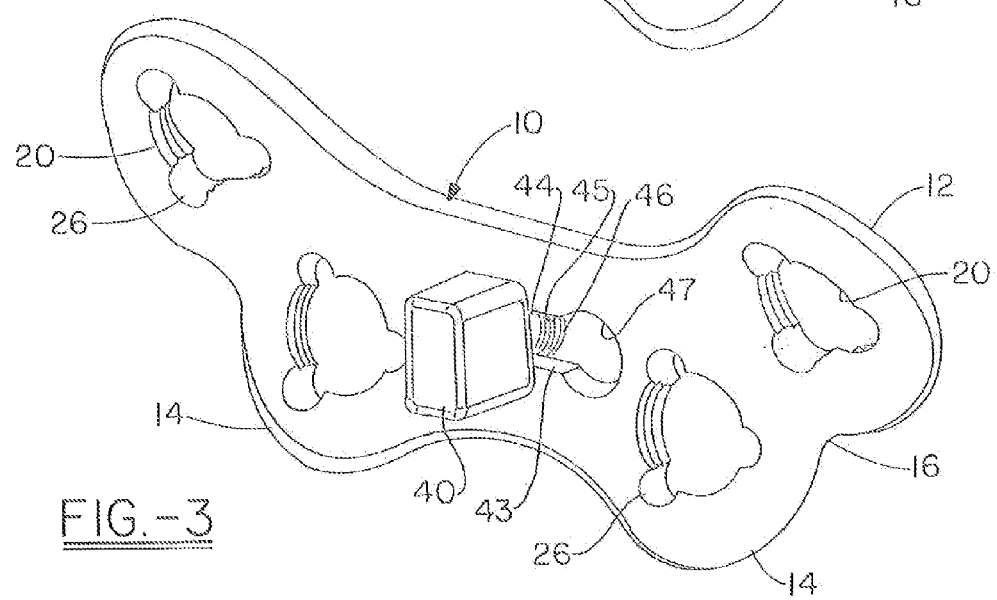
FIG. 3 is a back view of a modification of the embodiment of the osteotomy plate of FIGS. 1 and 2 showing a keyhole for attachment of the support member.

In the modification shown in FIG. 3, the central opening is a keyhole 43. In this version; the necked portion 44 of the support member 40 has a width that is smaller than the keyhole 43, and the stop 46 has a width that is greater than the slot 45, but which is smaller than the slot portion 45 of the keyhole 43 to enable the first support member to movably engage the plate and the stop 46 is smaller than the enlarged opening 47 in the keyhole 43 to allow the stop to be inserted through this area.

Figure 4:
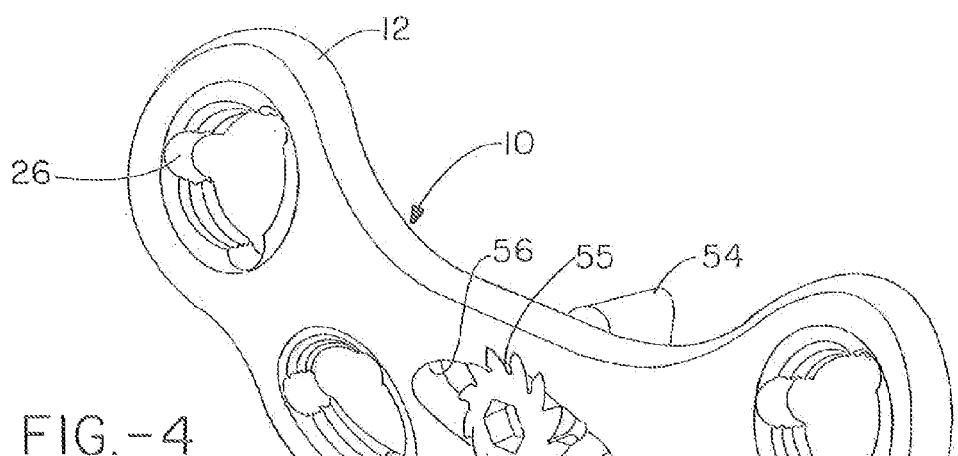
FIG. 4 is a further modification of the embodiment of the osteotomy plate of FIGS. 1 and 2.
Figure 5:
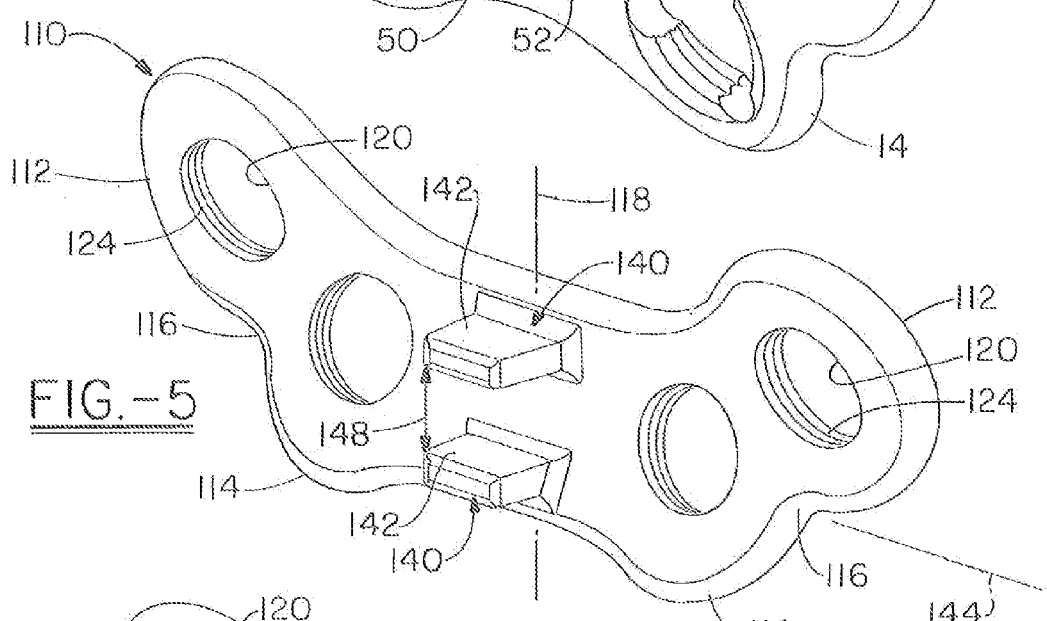
FIG. 5 is a second embodiment of the osteotomy plate shown in FIG. 1 having an integral support member which extends in the longitudinal direction.
Figure 6:
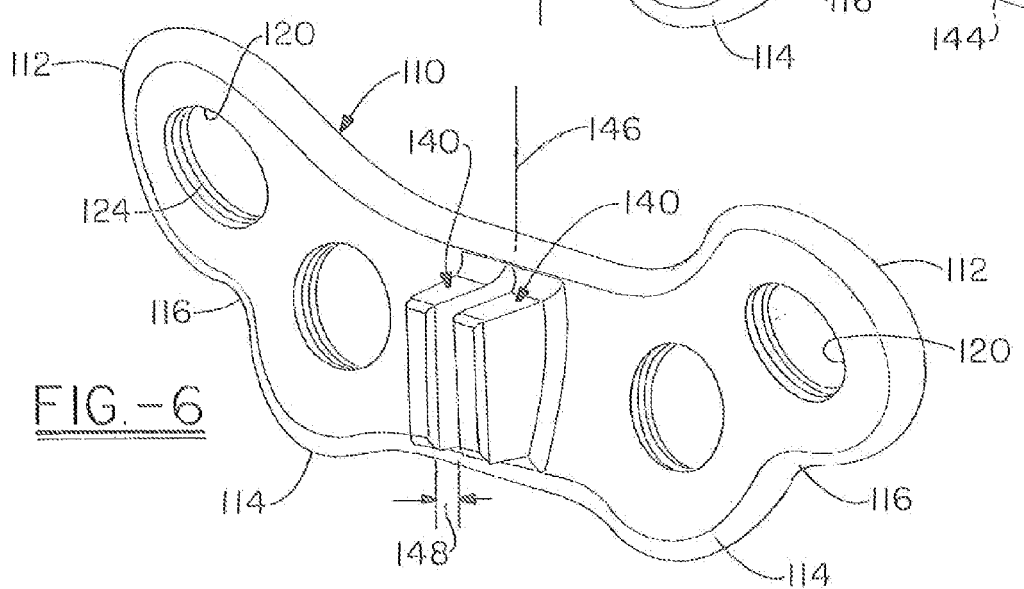
FIG. 6 is a modification of the osteotomy plate shown in FIG. 5 having an integral support member that extends transverse to the longitudinal direction.

In the ratcheting version of the present invention shown in FIG. 4, the stop is an round shape 50 that includes inverted teeth 52 which enable the elliptical support 54 to be used for distraction of the bone and to stop the backward rotation of the support when the stop 50 is engaged in a circular area 55 within the elliptical central opening 56.

In a second embodiment, the plate 110 has the same bilateral double tabbed footprint as the first embodiment, with a first set of tabs 112 or wings flanking a second set of tabs 114 or wings with a slight incurve 116 between the tab members on either side of the medial axis 118. Again, each tab includes an opening 120 for a screw or other fastening means and the openings 120 also include internal threads 124 which can selectably receive a fixed angle locking screw, a variable angle locking screw or a variable angle non-locking screw. In this embodiment, the bottom side of the plate 110 includes fixed support means 140 that are advantageously, a pair of flange members 142 that can extend parallel in the direction of either the long axis 144 or the medial axis 146 of the plate. The flanges define a channel 148, which allows for bone in-growth.

Figure 7:
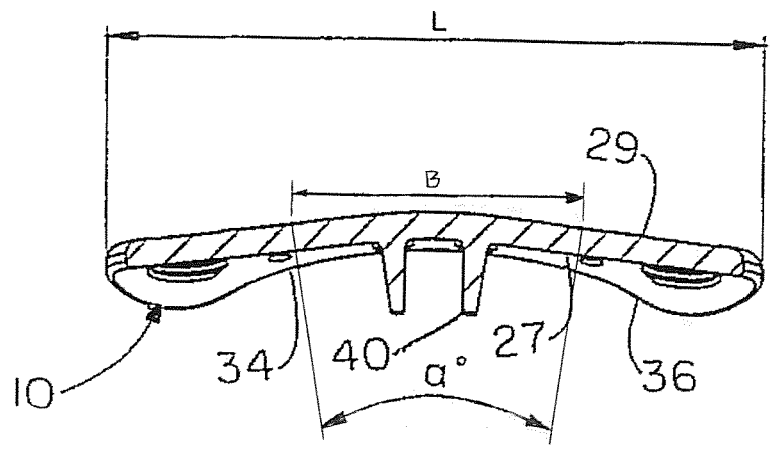
FIG. 7 is a cross sectional view of the osteotomy plate of FIG. 6 showing a bend along the longitudinal axis.

FIG. 7 illustrates the plate in cross-section along the longitudinal axis. As can be seen the plate has a generally uniform thickness between the inward surface 27 which opposes and optimally, but not necessarily engages the bones, and the outward surface 29. The inward surface 27 of the plate 10 includes a generally uniform radius of curvature 34, 36 along both the longitudinal axis in the transverse direction but in an advantageous modification of the invention, the plate includes a bend in the direction of the longitudinal axis in the area of the support member, and extending outward in either direction from there along the longitudinal axis, where the axis is again straight. The amount of bend B will depend on the length of this section of the plate. Preferably, the bend is limited to less than 75%, or more preferably to less than 66% or even 50% of the length of the plate along the longitudinal axis, with an angle of from about 3° to about 15° or 12°, of more specifically from about 3° to about 15° and more specifically yet of from about 5° to about 12°. If the length of this section is 1 mm, the bend, illustrated in FIG. 7 as α, is from about 1° to about 6°, and preferably about 2° to about 3°, with 3 mm being from about 4° to about 10°, and 5 mm being from about 5° to about 12.5°, and 7 mm being from about 6° to about 15°.

The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.25 and 1.75 millimeters, and most preferably between about 1.4 and 1.6 millimeters. The plate includes a continuous rounded outer edge 41, which is defined between the top and the bottom surface. In addition, the plate 10 can include a one or more small through holes sized to receive a K-wire or other similar guide wire.

While in accordance with the patent statutes the best mode and preferred embodiment have been set forth, the scope of the invention is not limited thereto, but rather by the scope of the attached claims.

What is claimed is:

1. An orthopedic opening osteotomy plate having a plate portion which has a butterfly shaped outline defining a long axis and a transverse short axis and exhibiting bilateral mirror symmetry about the short axis and comprising a central portion joined to a first pair and a second pair of longitudinally spaced tabs, the first pair of tabs on one side of the long axis and the second pair of tabs on the other side of the long axis, wherein the first set of longitudinally spaced tabs flank the second pair of longitudinally spaced tabs such that the respective tabs of each of the first and second pair of tabs are medially offset relative to each other, each of the tabs including a threaded screw hole having an axis, the plate further having a curve in the z direction about the long axis of the plate portion whereby the axes of the screw holes of the respective tabs on either side of the long axis converge but do not impinge and the plate further includes an osteotomy support that extends from the plate.

2. The orthopedic plate as set forth in claim 1 in which the osteotomy support is integral to the plate.

3. The orthopedic plate as set forth in claim 2 in which the osteotomy support comprises a block that extends from the plate transverse to the long axis of the plate portion.

4. The orthopedic plate as set forth in claim 3 in which the osteotomy support comprises a pair of flanges that further extend in the direction of the long axis of the plate portion and which define a channel therebetween.

5. The orthopedic plate as set forth in claim 3 in which the osteotomy support comprises a pair of flanges that further extend transverse to the direction of the long axis of the plate portion and which define a channel therebetween.

6. The orthopedic plate as set forth in claim 5 wherein the bend defines an angle between the flange members of between about 3° and about 15°.

7. The orthopedic plate as set forth in claim 1 in which the osteotomy support is modular to the plate.

8. The orthopedic plate as set forth in claim 7 in which the plate portion includes a central opening and the osteotomy support comprises a support member and a stop member where the stop member is captured in the central opening of the plate portion to join the osteotomy support to the plate portion.

9. The orthopedic plate as set forth in claim 8 in which the central opening includes a keyway having an opening with a wider diameter that opens to passage having a narrower diameter, and the stop includes a wider diameter member joined by a necked portion to the support member and the wider diameter member fits through the wider diameter opening in the central opening but not through the narrower diameter portion, and the necked portion is narrower than the narrower diameter passage so that the support can slide in the passage.

10. The orthopedic plate as set forth in claim 8 in which the osteotomy support comprises an ellipse.

11. The orthopedic plate as set forth in claim 8 in which the stop member further includes a high friction surface.

12. The orthopedic plate as set forth in claim 11 in which the high friction surface comprises teeth.

13. The orthopedic plate as set forth in claim 12 wherein the teeth are ratcheting teeth, and the central opening also forms an ellipse.

14. The orthopedic plate as set forth in claim 1 wherein the central portion of the plate includes a bend along the long axis in the z axis when viewed from the top.

15. The orthopedic plate as set forth in claim 14 wherein the length of the bend is limited to less than 75% of the length of the plate along the long axis.

16. The orthopedic plate as set forth in claim 15 wherein the length of the bend is limited to less than 66% of the length of the plate along the long axis.

17. The orthopedic plate as set forth in claim 15 wherein the length of the bend is limited to less than 50% of the length of the plate along the long axis.

* * * * *